United States Patent [19]

Bishop et al.

[11] Patent Number: 5,612,456

[45] Date of Patent: Mar. 18, 1997

[54] FACTOR XIII COMPOSITIONS

[75] Inventors: Paul D. Bishop, Fall City; Gerald W. Lasser, Everett; Mads Laustsen, Seattle; Jin-Jyi Chang, Issaquah, all of Wash.

[73] Assignee: ZymoGenetics, Inc., Seattle, Wash.

[21] Appl. No.: 333,236

[22] Filed: Nov. 2, 1994

Related U.S. Application Data

[63] Continuation of Ser. No. 927,196, Aug. 7, 1992, abandoned, which is a continuation-in-part of Ser. No. 741,263, Aug. 7, 1991, abandoned, which is a continuation-in-part of Ser. No. 270,714, Nov. 14, 1988, Pat. No. 5,204,447, and Ser. No. 525,556, May 18, 1990, abandoned, and Ser. No. 521,805, May 10, 1990, abandoned.

[51] Int. Cl.$^6$ .................... A61K 35/14; A61K 38/36; C07K 1/20; C07K 14/39
[52] U.S. Cl. .................... 530/381; 530/395; 530/412; 530/415; 530/416; 530/417
[58] Field of Search .................... 530/381, 395, 530/412, 415, 416, 417, 824, 830, 831, 834; 514/21, 2, 12

[56] References Cited

U.S. PATENT DOCUMENTS

| | | | |
|---|---|---|---|
| 3,904,751 | 9/1975 | Zwisler et al. | 530/381 |
| 3,931,399 | 1/1976 | Bohn et al. | 530/381 |
| 4,285,933 | 8/1981 | Fukushima et al. | 530/381 |
| 4,597,899 | 7/1986 | Falke | 530/383 |
| 5,047,506 | 9/1991 | Lobermann et al. | 530/381 |

FOREIGN PATENT DOCUMENTS

| | | | |
|---|---|---|---|
| 69896/87 | 9/1987 | Australia | C12N 15/00 |
| 0268772 | 6/1988 | European Pat. Off. | |
| 278416 | 8/1988 | European Pat. Off. | A61K 35/16 |
| 330049 | 8/1989 | European Pat. Off. | A61K 37/02 |
| 2247199 | 10/1990 | Japan | C07K 15/06 |
| WO90/05777 | 5/1990 | WIPO | C12N 9/10 |

OTHER PUBLICATIONS

McDonagh, et al., Biochim. Biophys. Acta 446, 345–357 (1976).
Schwartz, et al., J. Biol. Chem. 246, 5851–5854 (1971).
Cook and Holbrook, "The Calcium–Induced Dissociation of Human Plasma Clotting Factor XIII", *Biochem. J.* 141:79–84, 1974.
Curtis and Lorand, "Fibrin–Stabilizing Factor (Factor XIII)", *Methods Enzymol.* 45:177–191, 1976.
*Separation News*, "A Strategy for protein purification", vol. 13.6, Pharmacia, 1986.
Harris et al., "Protein Purification Methods", IRL Press, pp. 51–64, 222–231, 154–157, 1989.
Sofer et al., BioTechniques, pp. 198–203, Nov./Dec. 1983.
Kato et al., Adv. Chromatography, vol. 26, pp. 97–115, 1987.
Scopes, Robert K., "Protein Purification", Second Edition, Springer–Verlag, pp. 178–181 and Chapter 3, 1987.

*Primary Examiner*—Chhaya D. Sayala
*Attorney, Agent, or Firm*—Jeffrey J. King

[57] ABSTRACT

Highly purified factor XIII and methods of purifying factor XIII are disclosed. Factor XIII is purified from a biological fluid, such as a cell lysate. The methods provide factor XIII compositions that are greater than 99% pure with respect to contaminating proteins. The methods further provide factor XIII compositions wherein 1% or less of the factor XIII is activated factor XIII.

21 Claims, 3 Drawing Sheets

FACTOR XIII COMPOSITIONS

CROSS-REFERENCE TO RELATED APPLICATIONS

This application is a continuation of U.S. patent application Ser. No. 07/927,196, filed Aug. 7, 1992, now abandoned, which is a continuation-in-part of Ser. No. 07/741,263, filed Aug. 7, 1991, now abandoned, which is a continuation-in-part of Ser. No. 07/270,714, filed Nov. 14, 1988, now U.S. Pat. No. 5,204,447, and of Ser. No. 07/525,556, filed May 18, 1990, which application has been abandoned and is a continuation-in-part of U.S. Ser. No. 07/521,805, filed May 10, 1990 which has been abandoned.

TECHNICAL FIELD

The present invention relates to methods of protein purification in general, and more specifically to purified factor XIII and to methods for purifying factor XIII from a variety of biological fluids.

BACKGROUND OF THE INVENTION

Factor XIII (also known as fibrin stabilizing factor, fibrinoligase, or plasma transglutaminase) is a plasma glycoprotein that circulates in blood as a zymogen ($M_r$=~320 kD) complexed with fibrinogen (Greenberg and Shuman, *J. Biol. Chem.* 257: 609614 6101, 1982). Plasma factor XIII zymogen is a tetramer consisting of two a subunits ($M_r$=~75 kD) and two b subunits ($M_r$=~80 kD) (Chung et al., *J. Biol. Chem.* 249: 940–950, 1974) having an overall structure designated as $a_2b_2$. The a subunit contains the catalytic site of the enzyme, while the b subunit is thought to stabilize the a subunit or to regulate the activation of factor XIII (Folk and Finlayson, *Adv. Prot. Chem.* 31: 1–133, 1977; Lorand et al., *Biochem. Biophys. Res. Comm.* 56: 914–922, 1974). The amino acid sequences of the a and b subunits are known (Ichinose et al., *Biochemistry* 25: 6900–6906, 1986; Ichinose et al., *Biochemistry* 25: 4633–4638, 1986). Factor XIII occurs in placenta and platelets as an $a_2$ homodimer.

In vivo, activated factor XIII (factor XIIIa) catalyzes cross-linking reactions between other protein molecules. During the final stages of blood coagulation, thrombin converts factor XIII zymogen to an intermediate form ($a'_2b_2$), which then dissociates in the presence of calcium ions to produce factor XIIIa, a homodimer of a' subunits. Placental factor XIII is activated upon cleavage by thrombin. Factor XIIIa is a transglutaminase that catalyzes the cross-linking of fibrin polymers through the formation of intermolecular $\xi(\delta$-glutamyl) lysine bonds, thereby increasing clot strength (Chen and Doolittle, *Proc. Natl. Acad. Sci. USA* 66: 472–479, 1970; Pisano et al., *Ann. N.Y. Acad. Sci.* 202: 98–113, 1972). This cross-linking reaction requires the presence of calcium ions (Lorand et al., *Prog. Hemost. Throm.* 5: 245–290, 1980; Folk and Finlayson, *Adv. Prot. Chem.* 31: 1–133, 1977). Factor XIIIa also catalyzes the cross-linking of the δ-chain of fibrin to $\alpha_2$-plasmin inhibitor and fibronectin, as well as the cross-linking of collagen and fibronectin, which may be related to wound healing (Sakata and Aoki, *J. Clin. Invest.* 65: 290–297, 1980; Mosher, *J. Biol. Chem*, 250: 6614–6621, 1975; Mosher and Chad, *J. Clin. Invest.* 64.: 781–787, 1979; Folk and Finlayson, ibid.; Lorand et al., ibid.). The covalent incorporation of $\alpha_2$-plasmin inhibitor into the fibrin network may increase the resistance of the clot to lysis (Lorand et al., ibid.).

Factor XIII deficiency results in "delayed bleeding," but does not affect primary hemostasis (Lorand et al., ibid.) Current treatment practices for patients having factor XIII deficiencies generally involve replacement therapy with plasma or plasma derivatives, or with a crude placental factor XIII concentrate (Lorand et al., ibid.; Forbisch et al., *Dtsch. med. WochenSchr.* 97: 449–502, 1972; Kuratsuji et al., *Haemostasis* 11: 229–234, 1982).

Factor XIII is also useful in treatment of patients with disorders in postoperative wound healing (Mishima et al., *Chirurg* 55: 803–808, 1984; Baer et al., *Zentrabl. Chir.* 105: 642–651, 1980), scleroderma (Delbarre et al., *Lancet* 2: 204, 1984; Guillevin et al., *La Presse Medicale* 14: 2327–2329, 1985; Guillevin et al., *Pharmatherapeutica* 4: 76–80, 1985; and Grivaux and Pieron, *Rev. Pnemnol. Clin.* 43: 102–103 1987), ulcerative colitis (Suzuki and Takamura, *Throm. Haeostas,* 58: 509, 1987), colitis pseudomembranous (Kuratsuji et al., *Haemostasis* 11: 229–234, 1982) and as a prophylactic of rebleeding in patients with subarachnoid hemmorhage (Henze et al., *Thromb. Haemostas.* 58: 513, 1987). Furthermore, Factor XIII has been used as a component of tissue adhesives (U.S. Pat. Nos. 4,414,976; 4,453,939; 4,377,572; 4,362,567; 4,298,598; 4,265,233 and U.K. Patent No. 2 102 811 B).

A number of purification schemes for factor XIII have been described. Chung and Folk (*J. Biol. Chem.* 247: 2798–2807, 1972) prepared factor XIII from platelet-concentrated plasma or from a fibrinogen preparation. Cooke and Holbrook (*Biochem. J.* 141: 79–84, 1974) describe the purification of factor XIII from the Cohn-I fraction. The method involves multiple ammonium sulfate precipitation steps and fractionation on DEAE cellulose chromatography to purify factor XIII from plasma. Skrzynia et al. (*Blood* 60: 1089–1095, 1985) purified the a subunit of factor XIII from a placental concentrate by chromatography and ammonium sulfate precipitation. Zwisler et al. (U.S. Pat. No. 3,904,751) and Bohn et al. (U.S. Pat. No. 3,931,399) describe multistep isolation procedures which rely on the use of diaminoethoxy-acridine lactate to precipitate factor XIII. This precipitating agent would be an unacceptable contaminant in a therapeutic composition. Falke (U.S. Pat. No. 4,597,899) describes the isolation of factor XIII from an extract of placenta by alcohol precipitation.

Many of the previously described methods for purifying factor XIII have been directed to isolating it from plasma, serum, or fractions thereof. These starting materials are already enriched for factor XIII, and the contaminating proteins are generally well characterized and removable by known methods. Moreover, many of the known factor XIII-based therapeutic compositions are plasma fractions that have been enriched for factor XIII and contain other plasma proteins such as fibrinogen and fibronectin. Consequently, previously described purification or enrichment schemes are poorly suited to preparing highly purified factor XIII from heterogeneous starting materials, including crude cell lysates, where contaminating proteolytic activity may be high or unacceptable contaminants may be present. Furthermore, many of these methods were developed for laboratory-scale purification and are difficult to scale up for economical preparation of therapeutic quantities of factor XIII.

There is therefore a need in the art for simple, economical methods for purifying factor XIII. There is a further need in the art for purification methods that provide factor XIII preparations having low levels of factor XIIIa. Such methods should lend themselves to large-scale production of highly purified factor XIII from crude starting materials, such as lysates of recombinant cells. The present invention provides such methods, together with other, related advantages.

DISCLOSURE OF THE INVENTION

The present invention provides highly purified factor XIII compositions and methods for producing highly purified factor XIII. Using the methods disclosed, factor XIII that is at least 99% pure with respect to contaminating proteins may be obtained. These methods are particularly suited to purification of recombinant factor XIII, including yeast-produced recombinant human factor XIII. Within one embodiment, compositions of yeast-produced recombinant factor XIII containing less than 100 parts per million (ppm) of yeast protein are obtained. Within related embodiments, compositions containing less than 50 ppm, less than 20 ppm, less than 10 ppm and less than 1 ppm of yeast protein are obtained. Within additional embodiments, compositions are obtained wherein 1% or less of the factor XIII is factor XIIIa, as well as compositions wherein 0.5% or less of the factor XIII is factor XIIIa. These highly purified factor XIII compositions are suitable for use in pharmaceutical compositions, such as tissue adhesives.

The methods of the present invention are generally characterized by use of one or more crystallization steps, in which factor XIII is isolated from a biological fluid through the formation of a crystalline factor XIII precipitate, which is subsequently recovered. Within one embodiment, the purification comprises the steps of (a) fractionating a biological fluid by anion exchange chromatography to produce a fraction enriched for factor XIII, (b) adding Na-acetate to the enriched fraction to form a crystalline precipitate, (c) dissolving the precipitate to form a solution, (d) fractionating the solution by hydrophobic interaction chromatography to produce a second fraction enriched for factor XIII, (e) fractionating the second enriched fraction by anion exchange chromatography to produce a third fraction enriched for factor XIII, (f) adjusting the pH of the third enriched fraction to pH 5.2–6.5 to produce a factor XIII-containing precipitate, (g) recovering said precipitate, (h) dissolving the precipitate to form a solution, and (i) fractionating the solution by gel filtration and collecting a factor XIII-containing peak fraction. Within a preferred embodiment, the step of adjusting the pH comprises addition of succinic acid to the enriched fraction. Within a related embodiment, factor XIII is purified from a biological fluid by as process comprising the steps of (a) fractionating a biological fluid by anion exchange chromatography to produce a fraction enriched for factor XIII, (b) adding Na-acetate to the enriched fraction to form a crystalline precipitate, (c) dissolving the precipitate to form a solution, (d) fractionating the solution by anion exchange chromatography to produce a second fraction enriched for factor XIII, (e) fractionating the second enriched fraction by hydrophobic interaction chromatography to produce a third fraction enriched for factor XIII, (f) fractionating the third enriched fraction by hydrophobic interaction chromatography to produce a fourth fraction enriched for factor XIII, and (g) fractionating the fourth enriched fraction by gel filtration and collecting a factor XIII-containing peak fraction.

These and other aspects of the invention will become evident upon reference to the following detailed description and the attached drawings.

DETAILED DESCRIPTION OF THE INVENTION

Figure 1:
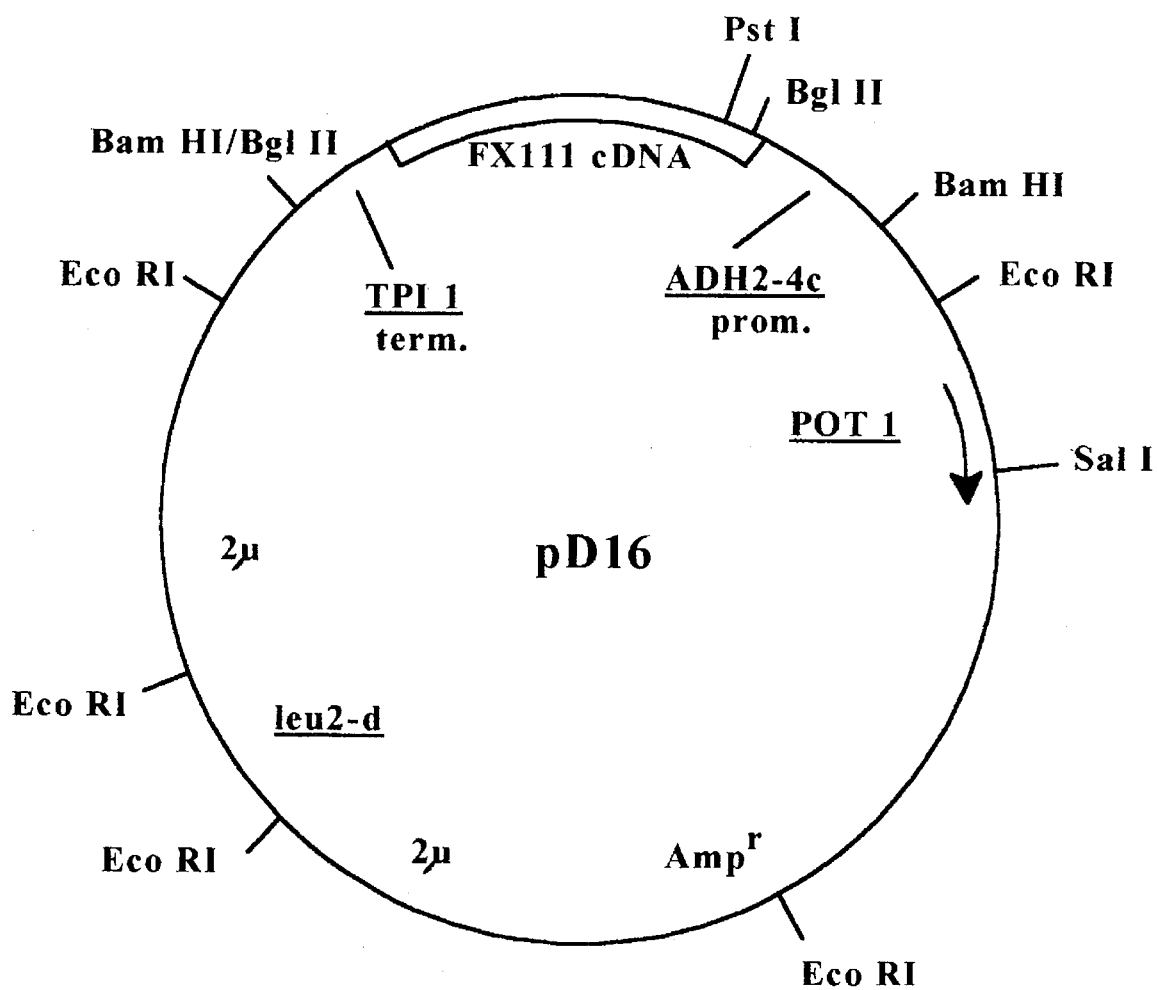
FIG. 1 illustrates the plasmid pD16.

Prior to setting forth the invention, it may be beneficial for an understanding thereof to define certain terms used hereinafter.

Factor XIII: The term "factor XIII" includes the complete factor XIII zymogen tetramer, the $a'_2b_2$ intermediate and factor XIIIa, as well as subunits thereof, including the a subunit, the a' subunit and $a_2$ dimers.

Biological fluid: Any fluid derived from or containing cells, cell components or cell products. Biological fluids include, but are not limited to, cell culture supernatants, cell lysates, cleared cell lysates, cell extracts, tissue extracts, blood, plasma, serum, and fractions thereof.

Precipitating aqent: A compound which, when added to a solution, causes another compound to precipitate from the solution. The precipitation may be due to the formation of a complex between the precipitating agent and the other compound or a phase change resulting in insolubility. Precipitating agents include organic modifiers e.g., ethanol, propanol, polyethylene glycol, and salts, such as ammonium sulfate.

Buffer: A substance that prevents appreciable changes of pH in solutions to which small amounts of acids or bases are added. A buffer generally comprises a combination of the proton-donor and proton-acceptor forms of a weak acid or weak base. Addition of small amounts of acid or base to a buffered solution shifts the equilibrium between the proton donor and proton acceptor. This equilibrium shift stabilizes the pH.

The present invention provides compositions of factor XIII that are greater than 99% pure with respect to contaminating proteins. According to the present invention, factor XIII is purified from a variety of biological fluids, including lysates or extracts of cells which naturally produce factor XIII in recoverable amounts, such as placental cells, as well as blood and blood fractions. Lysates and extracts of such cells and tissues may be prepared by a variety of procedures known in the art. However, due to the risk of viral contamination of blood and tissues, fluids derived from virus-free cells or cell lines that have been genetically modified to produce factor XIII are preferred sources. Particularly preferred biological fluids in this regard include lysates and cleared lysates of yeast cells that have been transformed to produce factor XIII, although in principle, any cell type capable of expressing cloned DNA sequences may be used. For example, the methods of the present invention can be used to produce recombinant factor XIII preparations from yeast cell lysates wherein the preparations contain significantly less than 10 ppm of yeast protein. Such contaminant levels are within the limits established for human drugs. Levels of contaminating proteins are assayed by conventional techniques (e.g. ELISA). The methods of the present invention are thus particularly well suited to the preparation of factor XIII for use in pharmaceutical preparations.

The purification methods of the present invention provide the additional advantage of removing activated factor XIII (factor XIIIa). It has been found in the inventors' laboratory that preparations of factor XIII containing 5–6% factor XIIIa are lethal when injected into laboratory animals. It is therefore important that preparations of factor XIII for systemic therapy contain not more than 1% factor XIIIa, preferably no more than 0.5% factor XIIIa. Such compositions are suited for long-term, high dose, systemic administration to patients.

Within the present invention, it has been found that factor XIII has low solubility in low ionic strength solutions having a pH at or about its isoelectric point (i.e., approximately 5.8), allowing separation of factor XIII from a solution without the need for precipitating agents. Thus, according to the present invention, factor XIII is isolated from a biological fluid by adjusting the pH of the fluid to about pH 5.2 to 6.5, such as by buffer exchange or acidification, to form a crystalline precipitate. Such a precipitation step has been found to provide a surprisingly high degree of purification of factor XIII. When used in combination with one or more chromatographic separation steps, precipitation at or about the isoelectric point has been found to result in factor XIII preparations that are greater than 99% pure.

Within a preferred embodiment, the above-described precipitation step is combined with a crystallization step, wherein Na-acetate is added to a factor XIII-containing solution, causing the crystallization of the factor XIII. The crystals are recovered by conventional means, such as centrifugation or filtration.

As noted above, recombinant cells and cell lines are preferred sources of factor XIII. Human and bovine factor XIII cDNA clones and production of factor XIII in recombinant cells, including bacteria, yeast and cultured mammalian cells, has been described by Grundmann et al. (published Australian patent application 69896/87) and Davie et al. (U.S. patent application Ser. No. 07/174,287; EP 268, 772), which are incorporated herein by reference. Particularly preferred host cells for producing recombinant factor XIII include yeasts, such as bakers' yeast (*Saccharomyces cerevisiae*) and species of *Pichia* and *Kluyveromvces*. Methods for expressing cloned DNA sequences are well known in the art. Briefly, a DNA sequence encoding factor XIII is operably linked to suitable promoter and terminator sequences in a vector compatible with the chosen host cell. The vector is then inserted into the host cell and the resulting recombinant cells are cultured to produce factor XIII. Depending on the particular host cell and the expression unit utilized, the factor XIII may either be secreted from the cell or retained in the cytoplasm.

When using cells that do not secrete the factor XIII, the cells are removed from the culture medium (e.g., by centrifugation) and treated to produce a lysate. Typically, yeast cells are treated by mechanical disruption using glass beads to produce a crude lysate. Preferably, the crude lysate is centrifuged, and the supernatant fraction is recovered. The supernatant is treated to produce a cleared lysate, typically by centrifugation at moderate speed (e.g., 10,000 x g) or filtration through a high molecular weight cutoff membrane.

When working with crude cell lysates, which are likely to contain high levels of proteases, it is preferred to minimize the time in which the lysate is in a concentrated form. This can be readily achieved by quickly diluting the lysate, preferably in cool (2°–5° C.) water. In general, the lysate will be diluted about 3- to 10-fold relative to the starting cell slurry. Factor XIII may also be obtained from cells that secrete it into the culture medium. Cells are transformed to express factor XIII subunits with an attached secretory signal sequence, which is removed from the factor XIII protein by proteolysis as it transits the secretory pathway of the host cell. For purification of the factor XIII, the cells are removed by centrifugation, the medium is fractionated, and the factor XIII is recovered.

When working with biological fluids containing complex mixtures of proteins, it is generally preferred to first fractionate the biological fluid by anion exchange chromatography, to produce an enriched fraction. Typically, a clarified biological fluid is passed over a column of an anion exchange medium at neutral to slightly alkaline pH and eluted using a suitable elution buffer. Suitable anion exchange media include derivatized dextrans, agarose, cellulose, polyacrylamide, specialty silicas, etc. PEI, DEAE, QAE and Q derivatives are preferred, with DEAE Fast-Flow Sepharose (Pharmacia, Piscataway, N.J.) being particularly preferred. As will be appreciated by those skilled in the art, fractionation can also be carried out in a batch process. Peak fractions (as determined by monitoring the absorbance of the eluate at 280 nm) are pooled for subsequent precipitation of factor XIII.

Although the enriched fraction from the anion exchange chromatography step may be subjected to precipitation at pH 5.2–6.5, it is preferred to apply several intervening purification steps, including crystallization, fractionation by hydrophobic interaction chromatography, and a second anion exchange chromatography step. Crystallization is carried out as described above by adding sodium acetate to a concentration of 9–18%, preferably about 11% by weight at a pH from about 6.2 to about 7.5. Crystallization is carried out at a temperature of 4°–25° C., preferably about 15° C. The crystalline precipitate is recovered, dissolved in a slightly alkaline buffer, and fractionated by hydrophobic interaction chromatography. Suitable chromatographic media in this regard include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins such as Amberchrom CG 71 (Toso Haas) and the like. In a typical purification protocol, a factor XIII solution is applied to a column of Phenyl-Sepharose FF, the column is washed with 20 mM sodium phosphate buffer, pH 7.4, containing 60 mS/cm NaCl and 2 mM EDTA. The factor XIII is eluted from the column with a descending salt gradient to 10 mM glycine, 1 mM EDTA, pH 7.4. Peak fractions are recovered, pooled, and applied to an anion exchange column. A variety of anion exchange media may be used, with Q-type resins being preferred. In a typical procedure, the peak fractions from the hydrophobic interaction chromatography step are applied to a column of Q-Sepharose FF (Pharmacia). The column is washed with 10 mM glycine, 20 mM sodium phosphate, 1 mM EDTA, pH 7.4, NaCl to 11 mS/cm. Factor XIII is eluted using a salt gradient to 10 mM glycine, 20 mM sodium phosphate, 1 mM EDTA, 0.25 M NaCl, pH 7.4.

Factor XIII is then precipitated by adjusting the pH of the factor XIII preparation as described above. In a preferred embodiment, the factor XIII preparation is acidified to a pH of 5.2–6.5, preferably about pH 5.4 to 6.2, most preferably about pH 5.8, by the addition of acid, such as succinic acid, citric acid, phosphoric acid or acetic acid. 0.2–0.5 M succinic acid is particularly preferred. The precipitate is then washed at pH 5.2 to 6.5, preferably about pH 5.4 to 6.2, most preferably about pH 5.8, and subsequent centrifugation, or by diafiltration against a pH 5.2 to 6.5 buffer using a 0.5 mm hollow fiber filter. Preferred buffers include 20–500 mM ammonium succinate solutions. It is preferred to include EDTA in the buffer at this step. Preferred buffers include 0.05 M ammonium succinate pH 5.8, 1.0% polyethylene glycol (PEG) 8000 USP, 0.005 M EDTA, 5 mM Na ascorbate; and 0.05 M ammonium succinate, 2 mM EDTA, 5 mM sodium ascorbate, pH 5.8. The buffer will generally correspond to the acid used in the acidification step (e.g. succinic acid-succinate buffer, citric acid-citrate buffer).

In an alternative embodiment, the enriched fraction from anion exchange chromatography is concentrated by precipitation with 40% saturated $(NH_4)_2SO_4$. The precipitate is dissolved in a small volume of buffer at a pH between about 7.0 and 8.0. The resulting solution is then dialyzed against a low ionic strength buffer at pH 5.2 to 6.5 to produce a crystalline precipitate. Buffers will generally be used at a concentration of between about 10 mM and 400 mM, preferably about 50 mM. Suitable buffers in this regard include low ionic strength solutions of heterocyclic polyamines, such as piperazine, spermidine, cadaverine and derivatives thereof, as well as MES, phosphate, ADA and Bis-Tris buffers adjusted to the desired pH. As used herein, the term "low ionic strength" includes solutions containing less than about 200 mM NaCl. The precipitate is recovered by centrifugation, redissolved and dialyzed a second time against the precipitation buffer.

Precipitation of factor XIII at pH 5.2 to 6.5 is facilitated by first concentrating the solution. Although the optimum concentration will depend to some extent on the buffer system, it is generally desired to work with factor XIII solutions of at least 0.2 mg/ml, preferably greater than 0.5 mg/ml, more preferably 2–25 mg/ml.

As will be evident to those skilled in the art, precipitation of factor XIII from other biological fluids will be carried out in substantially the same manner, i.e., by acidification or by dialyzing the fluid against the precipitation buffer to produce a precipitate.

Additional purification is achieved through the use of conventional chromatographic separation techniques, including ion exchange chromatography, hydrophobic interaction chromatography, immobilized metal chromatography and gel filtration. In a preferred embodiment, the precipitated factor XIII is dissolved in buffer to produce a solution, typically in a low ionic strength buffer at slightly alkaline pH, then fractionating the solution by gel filtration, such as by gel filtration on Sephacryl S-200 (Pharmacia) or the like. In a typical protocol, a 20 g/l solution of factor XIII in 10 mM glycine, 20 mM sodium phosphate, 1 mM EDTA, 10 mM NaCl is loaded on a Sephacryl S-200 column. Factor XIII is eluted from the column using the same buffer adjusted to 0.1 M NaCl. Peak fractions are collected, concentrated (e.g. by diafiltration), sterilized, and lyophilized. Prior to lyophilization, it is preferred to formulate the factor XIII in a phosphate buffered solution containing approximately 10 mM glycine or arginine, 0.1 mM EDTA, and 2% by weight sucrose, mannose or other non-reducing sugar and which provides a pH of approximately 7.8 upon reconstitution. Factor XIII prepared in this way is typically greater than 99% pure and pyrogen-free.

In the alternative, the pH 5.2–6.5 precipitation step may be replaced with a hydrophobic interaction chromatography step. Suitable chromatographic media in this regard include those derivatized with phenyl, butyl, or octyl groups and acrylic resins. Within a preferred embodiment, factor XIII is partially purified in a manner similar to that described above using a combination of anion exchange chromatography, sodium acetate crystallization, a second anion exchange chromatography step, and hydrophobic interaction chromatography. Peak fractions from the hydrophobic interaction chromatography step are pooled and fractionated on a second hydrophobic interaction chromatography column, such as a column of Amberchrom CG 71 (Toso Haas) or the like. Factor XIII is eluted from the column using a descending salt gradient. Peak fraction are pooled, gel filtered, concentrated and lyophilized for storage as described above. Factor XIII compositions prepared in this way contain minimal amounts of factor XIIIa, typically less than 0.3% of total factor XIII.

Within the above-described methods it is preferred to filter factor XIII solutions prior to each of the various chromatographic steps. Filtration is carried out using 0.45 µm or 0.2 µm filters.

Purity of factor XIII compositions prepared according to the present invention is monitored by conventional methods. Following individual separation steps, peak fractions may be identified by absorbance at 280 nm. Purified factor XIII may be quantitated by amino acid analysis, activity assay or the like. Factor XIIIa content may be measured by carrying out activity assays with and without thrombin treatment. Contamination of recombinant factor XIII preparations by host cell protein may be assayed by immunological methods, such as enzyme-linked immunoassay (ELISA). Such assays will be designed with levels of sensitivity suitable for use within the pharmaceutical art. For example, a sandwich-type ELISA assay of high sensitivity may be developed by optimization of antibody production and assay conditions. When testing for heterogeneous antigens, such as host antigens that would be present in a recombinant protein, it is preferred to use polyclonal antisera. Antigen is prepared from the host production organism by fermentation of untransformed cells and recovery of antigen. Typically, a yeast antigen is prepared by fermenting untransformed cells of the same strain as used for factor XIII production. The cells are harvested and lysed as in the isolation of factor XIII, and the lysate is used as an immunogen in female rabbits. Antisera are then recovered and pooled. When testing for pure antigen contaminants, monoclonal antibodies are preferred. The antisera or antibodies are purified, such as by purification on protein A followed by purification on either an antigen column (to retain the desired antibodies) or a product column (to remove cross-reacting antibodies). Antibodies or antisera are then screened and characterized for titer and selectivity. To optimize the signal to background ratio within the assay, the various components and conditions of the assay are investigated. These components and conditions include the type of plate to be used; coating conditions for the antisera; coated plate storage conditions; blocking and wash conditions, including blocking agent, time of blocking, and wash; sample capture conditions, including pH, ionic strength, temperature, incubation time and buffer; second antibody application conditions, including label, incubation time, pH and ionic strength; development conditions, including type of developing agent (e.g. horseradish peroxidase or alkaline peroxidase), temperature, time, optimum O.D.; and miscellaneous wash steps and conditions. Once conditions have been developed, the method is validated using spike-recovery studies of samples to assure accuracy of results. Selection and design of suitable assays is within the level of ordinary skill in the art.

Factor XIII prepared by the methods described herein may be used to produce pharmaceutical preparations, such as tissue adhesives, according to methods known in the art. Such preparations are described in, for example, U.S. Pat. No. 4,265,233 and published Australian Patent Application 75097/87, herein incorporated by reference.

The following examples are offered by way of illustration and not by way of limitation.

EXAMPLES

A cDNA encoding the a subunit of human factor XIII was cloned as previously described (Ichinose et al., *Biochemistry* 25: 6900–6906, 1986; Davie et al., U.S. patent application Ser. No. 07/174,287, which are incorporated herein by reference). The a subunit cDNA was used to construct a yeast expression vector, pD16 (FIG. 1). Briefly, pD16 is a *S. cerevisiae* 2-micron plasmid-based vector derived from pCPOT (ATCC No. 39685) as disclosed in U.S. patent application Ser. No. 07/525,556, which is incorporated herein by reference. It comprises an expression unit including the *S. cerevisiae* ADH2-4c promoter (published European Patent Application EP 284,044) and TPI1 terminator (U.S. Pat. No. 4,931,373) and a POT1 selectable marker (U.S. Pat. No. 4,931,373), which permits plasmid selection in glucose-containing media. The factor XIII and POT1 sequences are inserted in the vector in opposite transcriptional orientations (FIG. 1).

Example 1

A. Fermentation and Up-Stream Processing

Figure 2:
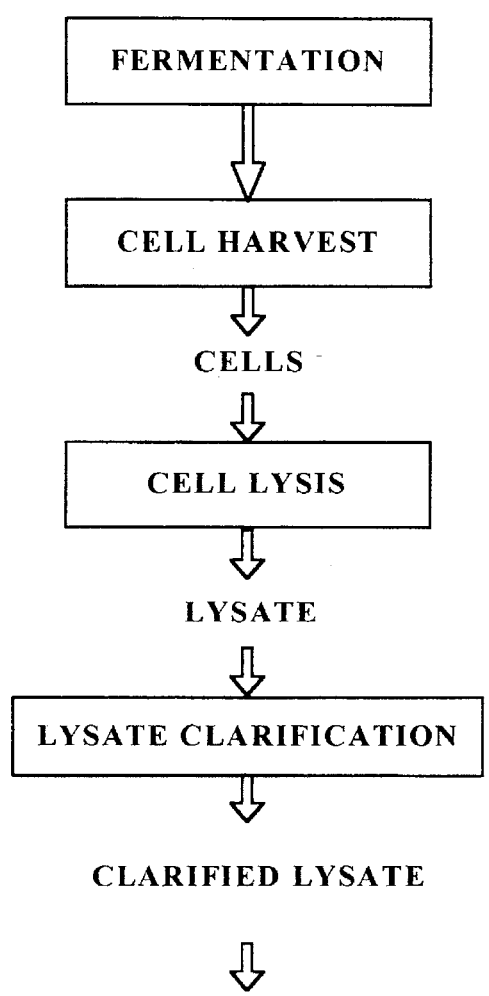
FIG. 2 is a flow chart summarizing a purification protocol for recombinant factor XIII produced in yeast cells.
Figure 2:
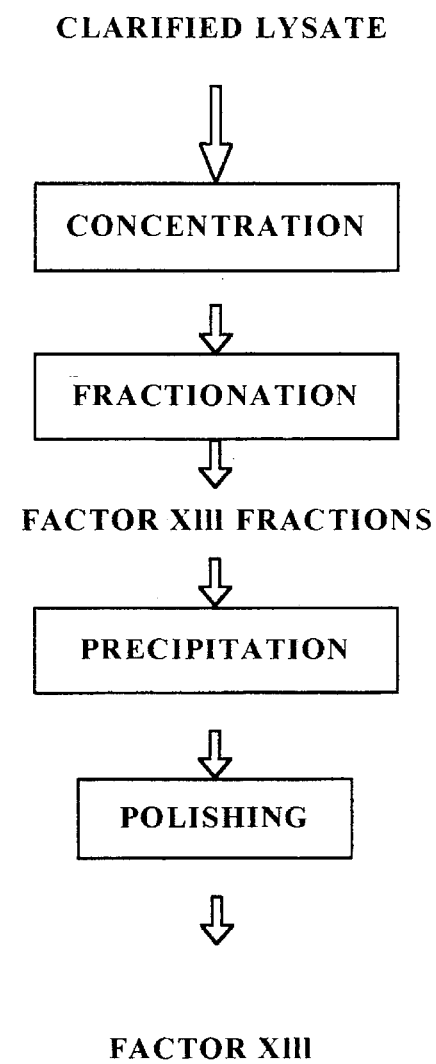

An exemplary method for purifying factor XIII from recombinant yeast cells is summarized in FIG. 2. Briefly, the cells are harvested and lysed, and the lysate is clarified. The clarified lysate is then concentrated and fractionated by chromatography. Factor XIII is precipitated from the factor XIII-containing fractions using piperazine, and a final polishing step is used to remove trace contaminants.

*Saccharomyces cerevisiae* strain ZM118 (a MATa/MATα diploid homozygous for leu2-3,112 ura3 tpil::URA3$^+$ bar1 pep4::URA3$^+$ [cir°]) was transformed with pD16. The transformed cells inoculated at approximately 0.1 g/l and cultured in a pH 5.5 medium containing 25 g/l yeast extract, 22.5 g/l (NH$_4$)$_2$SO$_4$, 6.5 g/l KH$_2$PO$_4$, 3 g/l MgSO$_4$ and 0.5% glucose with a glucose feed from 0 to 24 or 40 hours and an ethanol feed from 0 to 12 or 20 hours. The cultures (10 to 60 liters) were grown at 30° C. to a final cell density of approximately 60 g/l.

Cell cultures were harvested by concentration using a 0.2 μ cellulose ester hollow fiber cartridge (Microgon, Laguna Hills, Calif.). The final concentrate typically contained 600–3000 g wet weight of yeast cells (concentration >50% wet weight) in deionized H$_2$O.

The concentrated cells were then lysed. A maximum of 400 g (wet weight) of cells was diluted to 40% wet weight in lysis buffer (50 mM Tris HCl, pH 7.4, 150 mM NaCl, 15 mM EDTA, 5 mM 2-ME, 1 mM PMSF). The cells were lysed using a Dynomill (Glen Mills, Inc., Maywood, N.J.) in continuous flow mode. The cell suspension was combined with 0.5 liter of acid-washed 500 μ glass beads in a 0.6 liter container and lysed at 3000 rpm using a flow rate of 60–100 ml/min. to give an average residence time of 3–5 minutes. An additional one liter of buffer was pumped through the container.

The lysate was then clarified by centrifugation. One-liter bottles of lysate were centrifuged in a Sorvall RC-3B centrifuge at 5000 rpm in an H-6000A rotor for 45 minutes, and the pellets were discarded. The supernatant fractions were then conditioned by the addition of PMSF to a final concentration of 1 mM and 0.3 volume of 7% streptomycin sulfate. The mixture was then allowed to stand for 12 hours at 4° C. Final clarification was achieved by centrifugation in a Sorvall RC-5B centrifuge using 500 ml bottles in a GS-3 rotor at 7500 rpm for 90 minutes and/or 250 ml bottles in a GSA rotor at 12,000 rpm for 60 minutes. The resulting clarified lysate was then ready for down-stream processing.

B. Down-Stream Processing

The clarified lysate was fractionated by the addition of polyethylene glycol 1000 (PEG-1000) to a final concentration of 12% or PEG-8000 to a concentration of 8%. The mixture was incubated at 4° C. for 1 hour, then centrifuged using 500 ml bottles in a Sorvall GS-3 rotor at 7500 rpm for 90 minutes and/or 250 ml bottles in a GSA rotor at 12,000 rpm for 60 minutes. The precipitate was recovered.

Figure 3:
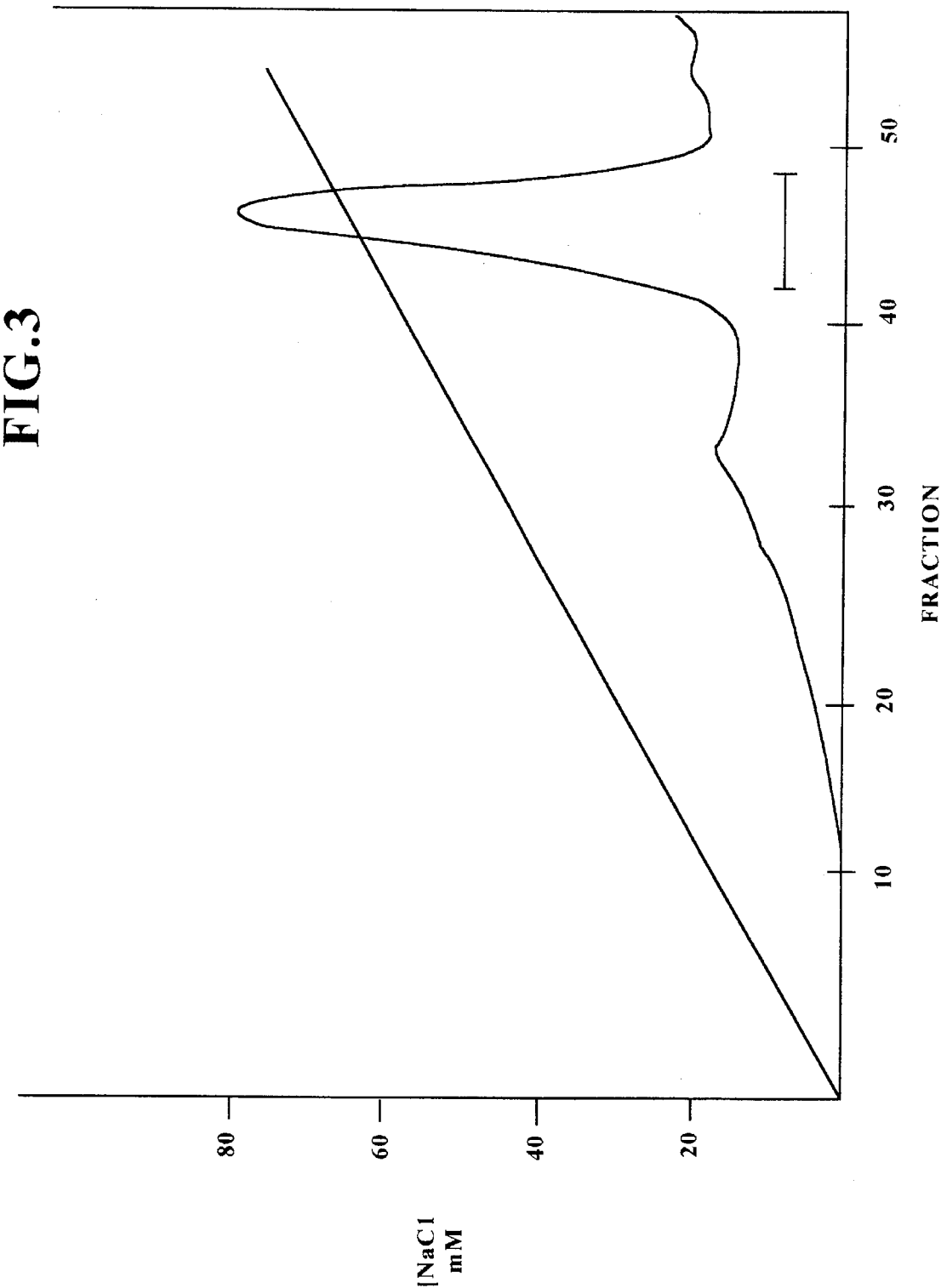
FIG. 3 illustrates a typical elution profile of factor XIII from DEAE fast-flow Sephadex. The bar indicates the fractions which were pooled for subsequent piperazine precipitation.

The PEG precipitate was dissolved in starting buffer (50 mM Tris-HCl, pH 7.8, 5 mM EDTA, 5 mM 2-ME, 0.5 mM PMSF), and the resulting solution was loaded on a 6×27 cm (500 ml) column of DEAE fast-flow Sephadex (Pharmacia). The column was washed with 1 l of starting buffer, and the factor XIII was eluted using a linear gradient of 1 l each of buffer A (50 mM imidazole, pH 6.3, 5 mM EDTA, 5 mM 2-ME) and buffer B (buffer A containing 150 mM NaCl). A typical elution profile is illustrated in FIG. 3. Fractions were assayed by measuring the incorporation of $^3$H-histamine into N, N-dimethyl casein or by ELISA. Pooled Factor XIII-containing fractions were precipitated by addition of (NH$_4$)$_2$SO$_4$ to 70% of saturation.

Factor XIII was then precipitated using piperazine buffer. The (NH$_4$)$_2$SO$_4$ mixture was centrifuged, and the supernatant fraction was discarded. The pellet was dissolved in 50 mM Tris, pH 8.0, 200 mM NaCl, 2.5 mM EDTA, 1 mM 2-ME, and dialyzed in 50 mM piperazine, pH 6.0, 5 mM EDTA, 5 mM 2-ME, 0.02% NaN$_3$ at 4° C. for about 5–12 hours. The mixture was then centrifuged at 5000 rpm for five minutes in a Sorvall RC-5B centrifuge using an SS-34 rotor. The resulting pellet was washed several times in fresh piperazine buffer.

Final purification was achieved by gel filtration. The piperazine pellet was resuspended in running buffer (50 mM Tris HCl, pH 8.0, 200 mM NaCl, 2.5 mM EDTA, 1 mM 2-ME) at a concentration of <100 mg precipitate per 20 ml buffer. The solution was dialyzed in running buffer for 5 hours at 4° C. and centrifuged to remove any residue. The dialyzed solution was then loaded onto a 4.5×80 cm (1270 ml) Sephadex S-200 column. The column was eluted with running buffer at 0.17 ml/minute. Factor XIII peak fractions were pooled.

Table 1 summarizes the purification steps described above. Yields were determined by a sandwich ELISA using a mouse monoclonal antibody to placental factor XIII and a rabbit polyclonal antibody. Yields may be underedstimated. Activity was determined by $^3$H-histamine incorporation.

TABLE 1

|  | Total Protein (g) | Total Activity (cpm × 10$^{-9}$) | Specific Activity (cpm/g × 10 − 9) | Step Yield (%) | Overall Yield (%) |
|---|---|---|---|---|---|
| Crude Lysate | 65 | 85 | 1.3 | 100 | 100 |
| Clarified Lysate | 34 | 91 | 2.7 | 107 | 107 |
| PEG ppt | 5.6 | 52 | 9.2 | 57 | 61 |
| DEAE (pH jump) | 0.72 | 26 | 37 | 50 | 31 |
| Piperazine ppt | 0.31 | 47 | 150 | 138 | 55 |
| S-200 |  |  | 168 | >68 | 37 |

Crude Lysate by ELISA . . . 480 mg total FXIII
Total Yield at Piperazine ppt . . . 65%

Example 2

Factor XIII, purified as described above, was dissolved in 50 mM Tris-HCl, pH 8.0, 200 mM NaCl, 2.5 mM EDTA, 1 mM 2-ME at a concentration of approximately 5.8 mg/ml. 0.5 mls aliquots of the resulting solution were pipetted into dialysis bags and dialyzed for two days at 4° C. in the following buffers:

50 mM MES (2-[N-Morpholino] ethanesulfonic acid), pH 6.1

50 mM PIP (Piperazine), pH 6.2

50 mM phosphate, pH 6.0

50 mM ADA (N-[2-Acetamido]-2-iminodiacetic acid), pH 6.0

50 mM Bis-Tris (bis[2-Hydroxyethyl]-imino-tris-[hydroxymethyl]methane), pH 6.1

Buffers were obtained from Sigma Chemical Co., St. Louis, Mo.

Following dialysis, the contents of the dialysis bags were centrifuged and the pellets and supernatants were assayed for factor XIII by the Bradford method using Protein Assay Reagent 23200 (Pierce Chemical CO.) as described by the manufacturer. The results, summarized in Table 2, indicate that factor XIII is insoluble in a variety of buffers at or about its isoelectric point.

TABLE 2

| Buffer | Gain in Volume(ml) | Absorbance Super | (595 nm) ppt | Concentration Super | (mg/ml) ppt |
|---|---|---|---|---|---|
| MES | .30 | .29 | .48 | .38 | .61 |
| PIP | −.10 | .22 | .26 | .28 | .33 |
| Phosphate | .50 | .25 | .50 | .31 | .64 |
| ADA | .20 | .33 | .49 | .41 | .62 |
| Bis-Tris | .30 | .23 | .49 | .29 | .62 |

Example 3

*Saccharomyces cerevisiae* strain ZM118 was transformed with pD16. The transformed cells were inoculated at approximately 0.1 g/l and cultured in a pH 5.5 medium containing 22.7 g/l yeast extract, 22.5 g/l (NH$_4$)$_2$SO$_4$, 6.5 g/l KH$_2$PO$_4$, 3 g/l MgSO$_4$.7H$_2$O, 0.5% glucose, trace elements and vitamins with a glucose feed for 39 hours. After 39 hours, 3.75 g/l ethanol was added over 1 hour, followed by an ethanol feed beginning at 2.5 g/l/hr. and increasing over 23 hours to a final rate of 3.75 g/l/hr. The pH of the culture was maintained at approximately 5.5 by the addition of 2M NaOH. The culture (approximately 60 liters) was grown at 30° C. for 63 hours to a final cell density of approximately 50 g/l.

Cell cultures were harvested by concentration using a 0.2 μ cellulose ester hollow fiber cartridge (Microgon, Laguna Hills, Calif.). The final concentrate typically contained 600–3000 g wet weight of yeast cells (concentration >50% wet weight) in deionized H$_2$O.

The concentrated cells were then lysed. A maximum of 400 g (wet weight) of cells was diluted to 40% wet weight in lysis buffer (50 mM Tris-HCl, pH 7.0, 150 mM NaCl, 5 mM EDTA, 10 mM 2-ME). 0.5 M PMSF in absolute ethanol was added to the cell slurry to a final concentration of 1 mM. The cells were lysed using a Dynomill (Glen Mills, Inc., Maywood, N.J.) in continuous flow mode. The Dynomill was pre-cooled to 0° C. or less, and all solutions were at 0°–8° C. The cell suspension was combined with 0.5 liter of acid-washed 500 μ glass beads in a 0.6 liter container and lysed at 3000 rpm using a flow rate of 150 ml/min. An additional one liter of lysis buffer was pumped through the container and added to the cell lysate. 0.5 M PMSF was added to a final concentration of 1 mM, and the pH of the lysate was adjusted to 7.8 with 2 M NaOH.

The lysate was then clarified by centrifugation. The pH was adjusted to 7.0 with 2 M HCl. The lysate was then centrifuged at 3895 x g at 4° C. for at least 40 minutes, and the pellets were discarded. The supernatant fractions were then concentrated and dialyzed against three volumes of 1x equilibration buffer (50 mM Tris pH 7.4, 10 mM 2-ME, 5 mM EDTA) to a conductivity of less than 5 mS/cm using a tangential flow system (Pellicon, Millipore, Bedford, Mass.) and 10 ft$^2$ of polysulfone membrane (PTHK, Millipore) with a 100 kD nominal molecular weight cutoff. Dialysis was carried out at 10° C. using an inlet pressure of 20–25 psi, an average transmembrane pressure of 4 psi, a flux of 400–500 ml/minute and a crossflow rate of approximately 20 liters/minute.

The concentrated, dialyzed lysate was then fractionated by chromatography on a column of DEAE Sepharose. A 23.5 cm high x 5.25 cm radius (2.0 liter) DEAE column was equilibrated with equilibration buffer until the conductivity was less than 4.5 mS/cm using a flow rate of approximately 45 ml/minute. The sample was loaded on the column at a flow rate of 16 ml/minute, then the column was washed with equilibration buffer until the absorbance of the eluate at 280 nm was less than 10% of the absorbance at full scale (full scale=0.5 AU). Factor XIII was eluted from the column with 0.12 M imidazole pH 5.8 containing 5 mM PMSF, 10 mM 2-ME and 5 mM EDTA. Peak fractions were pooled, adjusted to 5 mM PMSF and kept at 4° C. Pooled factor XIII-containing fractions were precipitated by addition of (NH$_4$)$_2$SO$_4$ to 40% of saturation.

Factor XIII was then precipitated using piperazine buffer. The (NH$_4$)$_2$SO$_4$ mixture was centrifuged at 3958 x g, and the supernatant fraction was discarded. The pellet was dissolved in a minimal volume of cold 25 mM Tris pH 7.4, 100 mM NaCl, 5 mM EDTA, 10 mM 2-ME, 0.19 M glycine, 0.02% NaN$_3$ (TAGS). The pH of the solution was maintained between 7.0 and 8.0 by the addition of 2 M Tris pH 7.5. The solution was centrifuged at 7649 x g to remove insoluble material. The supernatant was then dialyzed against 50 mM piperazine pH 5.8, 5 mM EDTA, 10 mM 2-ME, 0.02% NaN$_3$ overnight at 4° C. using 50,000 kD molecular weight cutoff dialysis tubing (Spectra/Por). The dialyzed solution was then centrifuged at 7649 x g for thirty minutes. The resulting pellet was redissolved in a minimal volume of cold TAGS, maintaining the pH as necessary by addition of 2 M Tris pH 7.8. The solution was again centrifuged, and the resulting supernatant was recovered and dialyzed against piperazine buffer overnight at 4° C. The solution was again centrifuged, and the pellet was dissolved in a minimal volume of TAGS as above.

Final purification was achieved by gel filtration. Factor XIII in TAGS (30 ml) was loaded onto a 1.5 liter (95 cm high x 2.25 cm radius) Sephacryl S-400 (Pharmacia) column. Separation was achieved using TAGS as the running buffer at a flow rate of 3.0 ml/min. Absorbance of the column eluate was monitored at 280 nm. The main factor XIII peak eluted between 1100–1350 ml. The peak fractions were pooled and concentrated by multiple centrifugations in a membrane concentrator (Centriprep, Amicon, Danvers, Mass.) to a final concentration of approximately 20 mg/ml.

The concentrate was then dialyzed overnight at 4° C. against 0.19 M glycine pH 7.4 containing 2% sucrose using 50,000 kD molecular weight cutoff dialysis tubing (Spectra/Por).

For storage, the dialyzed material was put through a 0.2 μ filter and aliquoted into vials. The samples were frozen quickly on a sheet of dry ice and stored at −80° C. Lyophilization of the frozen samples was carried out at −20° C. for 48 hours. The lyophilized factor XIII was sealed under argon and stored dessicated at −20° C.

Example 4

The *S. cerevisiae* ZM118/pD16 transformant strain was stored as a frozen seed stock in 2 ml aliquots. One aliquot was used to inoculate 0.7 l of FXIII S (Table 3). The culture was grown for 26 hours at 30° C. with shaking at 300 rpm.

TABLE 3

Media for Factor XIII Fermentations

| | |
|---|---|
| Factor XIII S (Leucine selective medium for inoculum preparation) | |
| (NH$_4$)$_2$SO$_4$ | 10.0 g/l |
| KH$_2$PO$_4$ | 5.0 g/l |
| MgSO$_4$ | 5.0 g/l |
| NaCl | 1.0 g/l |
| CaCl$_2$ | 0.5 g.l |
| amino acids I | 3.68 g/l |
| amino acids II | 3.68 g/l |
| citric acid | 4.29 g/l |
| trace metals | 10.0 ml/l |
| PPG-2025 | 0.1 ml/l |
| adjust pH to 5.0 and sterilize; before use 5 ml/l of vitamin G is added. | |
| Fermentation Medium | |
| yeast extract | 60 g/l |
| adjust pH to 5.0 and sterilize at 121° C., 30 min. after sterilization and cooling, add: | |
| salts | 10 ml/l |
| trace metals | 10 ml/l |
| vitamin G | 10 ml/l |
| PPG-2025 | 0.1 ml/l |
| Stock Solutions | |
| Amino acids I: | |
| adenine | 4.0 g |
| uracil | 3.0 g |
| L-tryptophane | 2.0 g |
| L-histidine | 8.0 g |
| L-arginine | 2.0 g |
| L-methionine | 2.0 g |
| L-tyrosine | 3.0 g |
| L-lysine | 3.0 g |
| L-phenylalanine | 5.0 g |
| combine as powder | |
| Amino Acids II: | |
| 5.0 g of each of the following L-amino acids: alanine, asparagine, aspartic acid, cysteine, glutamine, glutamic acid, glycine, isoleucine, proline, serine, threonine, valine. combine as powder | |
| Trace Metals: | |
| ZnCl$_2$ | 3.40 g |
| FeCl$_3$.6 H$_2$O | 27.00 g |
| MnCl$_2$.4 H$_2$O | 9.55 g |
| CuSO$_4$.5 H$_2$O | 1.10 g |
| CoCl$_2$ | 1.29 g |
| H$_3$BO$_3$ | 0.31 g |
| (NH$_4$)$_6$Mo$_7$O$_{24}$ | 0.01 g |
| KI | 0.01 g |
| dissolve in 4 l of distilled water, add 50 ml conc. HCl and adjust to 5.00 l with water. | |

TABLE 3-continued

Media for Factor XIII Fermentations

| | |
|---|---|
| Vitamin G: | |
| d-biotin | 5 mg |
| thiamine | 80 mg |
| pyridoxine | 80 mg |
| meso-inositol | 1500 mg |
| Ca pantothenate | 1500 mg |
| niacinamide | 60 mg |
| folic acid | 10 mg |
| riboflavin | 20 mg |
| choline | 100 mg |
| dissolve in 200 ml distilled water, pH 5.0 | |
| Salts: | |
| MgCl$_2$.6 H$_2$O | 250 g |
| CaCl$_2$.2 H$_2$O | 100 g |
| KCl | 100 g |
| dissolve in 2 M citric acid to 1000 ml | |

The inoculum culture was used to inoculate 7 l (nominal volume) of fermentation medium (Table 3). Fermentation was carried out for 63.5 hours using a glucose feed (21 ml/1 hour of 50% glucose/5% (NH$_4$)$_2$SO$_4$ for 19 hours, then increasing over 7 hours to 142.6 ml/hour) followed by an ethanol feed (58.7 ml/hour of 95% EtOH) beginning at 31 hours. The pH was maintained at 5.5 by addition of 4 M NH$_4$OH. Foaming was controlled with PPG-2000 (Union Carbide). The culture was agitated at 550–600 rpm. The vessel was maintained at 7.5 psi, a maximum O$_2$ partial pressure of 40% and DO$_2$>15%.

The culture was cooled to 20° C. and harvested as described in Example 3. 3.375 kg of wet packed cells were recovered.

The concentrated cells were then lysed. The concentrate was adjusted to 40% wet weight in 50 mM Tris-HCl pH 7.0, 150 mM NaCl, 5 mM EDTA, 10 mM 2-ME. The cells were then lysed in a Dynomill (Glen Mills, Inc.) essentially as described in Example 3. The lysate was then diluted 1:5 with deionized H$_2$O and clarified by centrifugation at 9,500 x g in a Sharples A3 centrifuge.

Initial fractionation was carried out on DEAE Fast Flow Sepharose (Pharmacia). The lysate was adjusted to <3 mS/cm conductivity and pH 7.2 by dilution with deionized H$_2$O. The column (2.5 l) was equilibrated with wash buffer (0.005 M EDTA, 0.05 M Tris-HCl pH 7.4, 0.01 M 2-ME), the lysate was loaded onto the column, and the column was washed with wash buffer. The column was eluted with 0.005 M EDTA, 0.01 M 2-ME, 0.12 M imidazole pH 5.8. Peak fractions from the DEAE column, which eluted at a pH of approximately 7.0, were pooled. A precipitate that formed spontaneously was recovered, resuspended in TAGS to ~20 mg/ml and dialyzed against TAGS overnight at 4° C. This material was then centrifuged at 12,000 x g for 15 minutes at 4° C. The supernatant was recovered and fractionated on a Sephacryl S-400 (Pharmacia) column as previously described. The purified factor XIII was then lyophilized for storage.

Ten mg of the lyophilized factor XIII was dissolved in 1 ml 10 mM potassium phosphate pH 7.8 containing 200 mM NaCl, 10 mM glycine and 10 mM 2-ME (buffer A). The solution was loaded onto a 10 ml phenylsepharose (Pharmacia) column. The column was washed for twelve minutes with buffer A. Protein was eluted from the column with a 40 minute linear gradient of buffer A and buffer B (10 mM glycine pH 7.8, 10 mM 2-ME). Fractions (1.75 ml) were collected. The factor XIII peak was contained in fractions 35–38. Fractions 36–38 (5.25 ml containing 5 mg factor XIII) were pooled. Factor XIII in 4 ml of the pool was crystallized by dialysis in 0.05 M ammonium succinate pH 5.8, 1.5% PEG 8000, 5 mM Na Ascorbate. The factor XIII was pelleted and redissolved in 1 ml 10 mM glycine pH 8 plus 20 μl 2 M Tris pH 8.

Example 5

Transformed yeast cells are fermented essentially as described in Example 4. The cells are concentrated and lysed, and the lysate is clarified by centrifugation.

Initial fractionation is carried out on DEAE Fast Flow Sepharose (Pharmacia) as described in Example 4. Peak fractions (as determined by $A_{280}$) are pooled and the pH is adjusted to 5.8 by the addition of 0.5 M succinic acid. The resulting factor XIII precipitate is recovered, washed with 0.05 M ammonium succinate, pH 5.8, 1.0% PEG 8000 USP (Union Carbide), 0.005 M EDTA, 0.01 M 2-ME, and the mixture is homogenized. The mixture is then centrifuged at 10,500 x g in a Sorvall RC-5B centrifuge equipped with an HB-4 rotor.

The precipitate is dissolved in 0.02 M phosphate buffer, pH 7.4, 0.3 M NaCl and loaded onto a phenyl-Sepharose (Pharmacia) column. The column is washed with the same buffer and eluted with 0.01 M glycine pH 7.4.

The $A_{280}$ peak from the phenyl-Sepharose column is pooled and dialyzed in TAGS. The dialyzed solution is then further purified by gel filtration on Sephacryl S-400 (Pharmacia) as described above. The factor XIII-containing peak fractions are collected, pooled, concentrated and dialyzed against 0.01 M glycine pH 7.4, 2% sucrose, 5 mM EDTA as described in Example 3. Samples are frozen, lyophilized, and stored dessicated and under argon at −20° C. Following gel filtration, yeast protein contamination is typically about 30 ppm or less by ELISA.

Example 6

A 1000 liter culture of S. cerevisiae ZM118/pD16 is fermented essentially as described in Example 4.

The cells are harvested by centrifugation using a Westfalia CSA-19 continuous flow centrifuge (Westfalia Separator AG, Oelde, Germany) at a flow rate of 11 liters/minute, 8150 rpm and a temperature of approximately 15° C. The time between shooting is 180 seconds. The vessel is flushed with pure water before each shot.

The resulting cell slurry is adjusted to 35–40% cells by volume with pure water, then adjusted to 30 mM Na-phosphate, 15 mM EDTA, 0.1 M NaCl, pH 7.8. The slurry is then lysed in a Dynomill KD 20 B homogenizer (Willy A. Bachofer AG, Basel) using 0.5 mm beads. The homogenizer is operated at 1200 rpm with a product flow rate of 4.8 liters/minute, keeping the inlet temperature below 10° C. The lysate from the homogenizer is added directly to pre-cooled (2°–5° C.) pure water to a final conductivity of 4.5+/−0.2 mS/cm, pH 7.2.

The diluted cell lysate is clarified using a Westfalia CSA-19 centrifuge at a flow rate of 7 liters/minute, 8150 rpm, and a temperature below 15° C. The time between shooting is 600 seconds. The resulting supernatant is filtered through Cuno model 12 ZP 3 filter equipped with a 45115-12-50S cartridge (Cuno, Inc., Meriden, CN).

The clarified lysate is then fractionated by anion exchange chromatography using a 10 cm long column of DEAE-Sepharose FF (Pharmacia, Piscataway, N.J.), 100 liter volume. The column is run at a flow rate of 6.5 liters/minute. After loading, the column is washed with 800 liters of 4.2 mS/cm Na-phosphate buffer, pH 7.2 containing 2 mM EDTA. Factor XIII is eluted from the column with 10 mS/cm sodium phosphate buffer, pH 6.3, containing 6 mM EDTA. The absorbance of the eluate at 280 nm is monitored, and peak fractions are pooled.

Factor XIII is crystallized from the pooled peak by addition of 12% w/v solid sodium acetate at pH 6.7. The solution is allowed to stand for 5–9 hours at 15°–20° C. The resulting crystalline precipitate is collected by centrifugation on a Sharples (Alfa-Laval Separation, Inc., Warminster, Pa.) AS-12V centrifuge at 15,000 rpm using a flow rate of 25–40 liters/hour. The precipitate is washed by suspending it in 10 mM Na-phosphate pH 6.7, 2 mM EDTA, 11% w/v Na-acetate for one hour, followed by centrifugation in a Sharples AS-12V centrifuge at 15,000 rpm and a flow rate of 15–25 liters/hour. The washed precipitate is dissolved in 100 liters of 10 mM Na-phosphate, 2 mM EDTA, 10 mM glycine, pH 8.0 at 5° C. over a period of at least four hours.

The dissolved, crystallized factor XIII is then filtered using a 0.45 micron filter and fractionated on a 25 cm long, 60 liter Phenyl-Sepharose FF (Pharmacia) column. The column is run at room temperature using a flow rate of 180 liters/hour. Conductivity of the factor XIII load is adjusted to 60 mS/cm by addition of NaCl, and pH is adjusted to 7.4 by addition of $H_3PO_4$. The column is washed with 5 column volumes of 60 mS/cm NaCl, 20 mM Na-phosphate, 2 mM EDTA, pH 7.4. Factor XIII is eluted using a gradient over 240 liters to 10 mM glycine, 1 mM EDTA, pH 7.4. The eluate is monitored at $A_{280}$.

The pooled peak fractions are filtered using a 0.2 micron filter, then further fractionated by chromatography on a 40-cm long, 30 liter Q-Sepharose FF (Pharmacia) column using a flow rate of 90 liters/hour. The starting material is adjusted to 11 mS/cm NaCl, pH 7.4. The column is washed with 150 liters of 10 mM glycine, 20 mM Na-phosphate, 1 mM EDTA, 11 mS/cm NaCl, pH 7.4. Factor XIII is eluted with a gradient over 240 liters to 10 mM glycine, 20 mM Na-phosphate, 1 mM EDTA, 0.25 M NaCl, pH 7.4. The eluate is monitored at $A_{280}$, and peak fractions are pooled.

The eluate peak from the Q-Sepharose column is concentrated on a 10,000 nominal molecular weight cutoff (NMWC) Hollow Fiber UF filter (AG Tech, Needham, Mass.) to 10–15 g/liter factor XIII.

The concentrated factor XIII is crystallized by adjusting the pH of the solution to 5.8 using 0.3 M succininic acid. The solution is stored overnight at 5° C., then centrifuged in a J 2-MI centrifuge (Beckman Instruments, Palo Alto, Calif.) for 20 minutes at 8000 rpm in a JA-10 rotor. The crystals are recovered and suspended in 0.05 M ammonium succinate, 2 mM EDTA, 5 mM sodium ascorbate, pH 5.8. The suspension is centrifuged in a Beckman J 2-MI centrifuge as above. The crystalline precipitate is recovered and resolubilized in 10 mM glycine, 20 mM Na-phosphate, 1 mM EDTA, 10 mM NaCl, pH 7.8 to a factor XIII concentration of 20 g/liter. The solution is centrifuged in a Beckman J 2-MI centrifuge as above, and the supernatant is collected.

Three-liter loads of the factor XIII concentrate are filtered using a 0.2 micron filter, then fractionated on 100 liters of Sephacryl S-200 (Pharmacia) (90 cm column length) using 20 mM Na-phosphate, 1 mM EDTA, 10 mM glycine, 0.1 M NaCl, pH 7.8. The eluate is monitored at $A_{280}$.

Peak fractions from the S-200 column are pooled and concentrated to 25 g factor XIII/liter by ultrafiltration using an AGT 10,000 NMWC Hollow Fiber UF filter and diafiltration with 10 volumes of 10 mM glycine, 0.1 mM EDTA, 2% sucrose, pH 7.4. The filtered solution is then sterilized by filtration through a 0.2 micron filter and lyophilized.

Factor XIII prepared essentially as described above was sampled at various points during the purification process and assayed for factor XIIIa content and yeast contamination. Factor XIIIa content was measured by means of a fluorometric assay. Factor XIII samples were prepared by diluting in 0.05 M bicine buffer pH 9.0 to a total volume of 200 μl per sample, keeping total protein below 20 μg. Samples were prepared in 10×10×48 mm cuvettes. To each cuvette was added 1.25 ml freshly prepared MDC-bicine cocktail (0.063 mM monodansylcadaverine (Sigma Chemical Co.) in 0.05 M bicine (N,N-bis[2-hydroxyethyl] glycine; Sigma) pH 9.0, prepared by dissolving 1.34 mg monodansylcadaverine in 0.5 ml 0.03 M HCl and mixing with an equal volume of 0.1 M Tris pH 7.4, then combining 0.4 ml of the solution with 24.0 ml 0.05 M bicine buffer, pH 9.0) and 50 μl 0.4 M $CaCl_2$. The solutions were mixed and prewarmed to 37° C. for 10 minutes. Fifty μl of 100 NIHU/ml thrombin was added to each cuvette, the solutions were gently mixed, and the cuvettes were incubated 10 minutes at 37° C. Fifty μl of freshly prepared dithiothreitol was added to each cuvette with gentle mixing. Two hundred μl 2% N,N-dimethyl casein was then added to each cuvette with gentle mixing, and the cuvettes were incubated 10 minutes at 37° C. Fifty μl of stop reagent (1.6 M ammonium sulfate, 0.2 M EDTA) was then added to each cuvette with gentle mixing. Fluorescence was measured in a Perkin-Elmer LS-5B fluorometer with excitation at 360 nm and emission at 500 nm using a slit width of 3 nm and a water bath temperature of 39° C. Blank was set using 200 μl bicine buffer in place of factor XIII and omitting stop reagent. Gain (100%) was set using a 50 μg recombinant factor XIII standard and omitting stop reagent. Results were compared to a standard curve constructed from 5, 10 and 25 μg/ml factor XIII standards produced by dilution of recombinant factor XIII quantitated by amino acid analysis. Factor XIIIa content of process samples was determined by assaying samples with and without thrombin. Following gel filtration on Sephacryl S-200, factor XIIIa content was reduced to approximately 0.3%. Factor XIIIa content of the dissolved lyophilized material was approximately 0.5%.

Yeast contamination was assayed by ELISA using a rabbit anti-yeast antibody. Sixteen 1-liter cultures of untransformed *S. cerevisiae* ZM118 were harvested, the cells were disrupted, and clarified lysates were prepared. Sixteen rabbits were immunized with this material, and antisera were prepared and pooled. The pooled antiserum was diluted to 10 μg/ml in ELISA buffer A (0.1 M sodium carbonate pH 9.6). One hundred μl of diluted antibody was added to each well of 96-well plates, and the plates were covered with plate sealer and stored overnight at 4° C. or for two hours at 37° C. Plates were then uncovered and washed five times with 200 μl per wash buffer C (phosphate buffered saline containing 0.1% Tween-20). Ten μl of yeast standard (pooled antigen) (2.8 mg/ml) was diluted to 2.8 μg/ml in buffer C. 28.6 μl of the diluted standard was added to 2.0 ml buffer C. The resultant working standard was serially diluted to obtain a standard curve of 40, 20, 10, 5, 2.5, 1.25 and 0.62 ng/ml. One hundred microliters of buffer C was added to three columns of each of rows B-H of a 96-well plate. One hundred microliters of yeast antigen working standard was added to each of three wells in row A. One hundred microliters of working standard was added to each of three wells in row B and, following thorough mixing, 100 μl from each well was transferred to row C. Serial dilution was continued in the three columns through row G, at which 100 μl of the diluted standard was removed from each well and discarded. 100 μl of buffer C was added to each well of two columns as blanks. Test samples were diluted in buffer C, and 100 μl of diluted samples were added to wells in triplicate. Plates were covered with plate sealer and incubated a minimum of 24 hours at room temperature. Just before use, biotinylated rabbit anti-yeast antibody (0.5 mg/ml stock) was diluted 1:100 in buffer C. The plates were drained and washed five times with with buffer C (200 μl per well), and 100 μl of diluted biotinylated antibody was added to each well. The plates were incubated at least 1.5 hours at 37° C, then washed five times with 200 μl/well buffer C. To each well was added 100 μl of streptavidin/HRP (Amersham) freshly diluted 1:1000 in buffer C. Plates were covered with plate sealer, incubated at 37° C. for 30–45 minutes, then washed five times with 200 μl/well buffer C. Two tablets (8 mg) OPD substrate (Sigma Chemical Co.) were dissolved in 10 ml OPD diluent (0.1 M Na citrate, pH 5.0). Just before use, 10 μl $H_2O_2$ was added to 10 ml of OPD substrate solution, then 100 μl of the solution was added to each well. The plates were incubated at room temperature until a yellow color developed (approximately 0.6–0.9 O.D. units), then 100 μl 2 M $H_2SO_4$ was added to each well to stop the reaction. Plates were read at 490 nm in a Molecular Devices (Mountain View, Calif.) plate reader. Results were compared to the standard curve using a segment having an O.D. greater than 0.015 at 490 nm and a coefficient of variation ≦15%. Yeast protein content was reduced to less than 1 ppm.

Example 7

Factor XIII was prepared essentially as described in Example 5 through crystallization with sodium acetate. The dissolved precipitate was adjusted to pH 7.4 with $H_3PO_4$ and to 11.2 mS/cm conductivity with NaCl.

The factor XIII solution was then fractionated on an 11-cm Q-Sepharose FF (Pharmacia) column. The column was loaded with 9 g factor XIII per liter of resin, then washed with 5 column volumes of 10 mM $Na_2HPO_4$, 10 mM glycine, 1 mM EDTA, pH to 7.4 with $H_3PO_4$, 11.2 mS/cm NaCl. Factor XIII was eluted using six column volumes of 10 mM $Na_2HPO_4$, 10 mM glycine, 1 mM EDTA, pH 7.4 with $H_3PO_4$, 0.25 M NaCl.

The $A_{280}$ peak from the Q-Sepharose column was then further fractionated on a 25 cm column of Toyopearl Butyl 650 at room temperature. The factor XIII solution was adjusted to pH 7.4 and 52 mS/cm with $Na_2SO_4$, and the column was loaded with 10 g factor XIII per liter of resin. The column was then washed with 20 mM $Na_2HPO_4$, 10 mM glycine, 1 mM EDTA, pH 7.5 with $H_3PO4$, 52 mS/cm with $Na_2SO_4$. Factor XIII was eluted with a gradient to 36 mS/cm of 1.5 column volumes of the same buffer adjusted to pH 7.4.

Peak fractions were recovered from the Butyl 650 column and assayed for factor XIIIa content and yeast protein as described in Example 5. Factor XIIIa content was 0.37%. Yeast protein contamination was 20 ppm.

Peak fractions from the Butyl 650 column were pooled and further fractionated on a 25 cm column of Amberchrom CG 71 resin. The column was run at room temperature. The eluant from the Butyl 650 column was diluted with pure water to 15 mS/cm, and the pH adjusted to 7.5. About twelve grams factor XIII were loaded per liter of resin. The column was washed with four column volumes 10 mM $Na_2HPO4$, 10 mM glycine, 1 mM EDTA, pH 7.5 with $H_3PO_4$, conductivity adjusted to 5.8 mS/cm with NaCl. Factor XIII was eluted from the column with a two column volume gradient of 10 mM glycine, 1 mM EDTA, pH 7.8 with $H_3PO_4$, to a conductivity 0.5 mS/cm.

The peak fractions from the Amberchrom column were assayed for Factor XIIIa content, which was found to be 0.06%, and yeast protein, which was <2.1 ppm.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for purifying factor XIII from a biological fluid, comprising the steps of:
   a) fractionating a biological fluid by anion exchange chromatography to produce a fraction enriched for factor XIII;
   b) adding Na-acetate to the enriched fraction to form a crystalline precipitate;
   c) dissolving the precipitate to form a solution;
   d) fractionating the solution by hydrophobic interaction chromatography to produce a second fraction enriched for factor XIII;
   e) fractionating the second enriched fraction by anion exchange chromatography to produce a third fraction enriched for factor XIII;
   f) adjusting the pH of the third enriched fraction to pH 5.2–6.5 to produce a factor XIII-containing precipitate;
   g) recovering said precipitate;
   h) dissolving the precipitate to form a solution; and
   i) fractionating the solution by gel filtration and collecting a factor XIII-containing peak fraction.

2. The method of claim 1 wherein the step of adjusting the pH comprises adding succinic acid to said third enriched fraction.

3. The method of claim 1 wherein said biological fluid is a yeast cell lysate.

4. The method of claim 1 wherein said factor XIII is human factor XIII.

5. The method of claim 1 wherein said factor XIII is recombinant human factor XIII.

6. The method of claim 1 wherein said factor XIII is a dimer of a subunits.

7. The method of claim 1 wherein the pH of the third enriched fraction is adjusted to 5.8 to produce a factor XIII-containing precipitate.

8. A method for purifying factor XIII from a biological fluid, comprising the steps of:
   a) fractionating a biological fluid by anion exchange chromatography to produce a fraction enriched for factor XIII;
   b) adding Na-acetate to the enriched fraction to form a crystalline precipitate;
   c) dissolving the precipitate to form a solution;
   d) fractionating the solution by anion exchange chromatography to produce a second fraction enriched for factor XIII;
   e) fractionating the second enriched fraction by hydrophobic interaction chromatography to produce a third fraction enriched for factor XIII;
   f) fractionating the third enriched fraction by hydrophobic interaction chromatography to produce a fourth fraction enriched for factor XIII; and
   g) fractionating the fourth enriched fraction by gel filtration and collecting a factor XIII-containing peak fraction.

9. A composition of matter comprising factor XIII which is at least 99% pure with respect to contaminating proteins and wherein 1% or less of said factor XIII is factor XIIIa.

10. The composition of claim 9 wherein said factor XIII is recombinant human factor XIII.

11. The composition of claim 10 wherein said recombinant human factor XIII is yeast-produced recombinant human factor XIII.

12. The composition of claim 11 wherein said composition contains less than 50 ppm of yeast protein.

13. The composition of claim 11 wherein said composition contains less than 20 ppm of yeast protein.

14. The composition of claim 11 wherein said composition contains less than 10 ppm of yeast protein.

15. The composition of claim 11 wherein said composition contains less than 1 ppm of yeast protein.

16. The composition of claim 15 wherein 0.5% or less of said factor XIII is factor XIIIa.

17. The composition of claim 9, wherein 0.5% or less of said factor XIII is factor XIIIa.

18. The composition of claim 9, wherein said factor XIII is human factor XIII.

19. The composition of claim 9, wherein said factor XIII is a dimer of a subunits.

20. A composition of matter comprising yeast-produced recombinant human factor XIII, wherein said composition contains less than 100 ppm yeast protein and wherein 1% or less of said factor XIII is factor XIIIa.

21. The composition of claim 20 wherein said composition contains less than 10 ppm yeast protein.

* * * * *